(12) United States Patent
Salnik et al.

(10) Patent No.: US 7,755,752 B1
(45) Date of Patent: Jul. 13, 2010

(54) COMBINED MODULATED OPTICAL REFLECTANCE AND PHOTOREFLECTANCE SYSTEM

(75) Inventors: Alexei Salnik, San Jose, CA (US); Lena Nicolaides, Castro Valley, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 12/098,979

(22) Filed: Apr. 7, 2008

(51) Int. Cl.
*G01N 21/00* (2006.01)

(52) U.S. Cl. .................................. 356/237.2; 356/237.6

(58) Field of Classification Search ... 356/237.2–237.6, 356/432, 369, 630, 73, 433, 445, 447, 319, 356/446; 324/752, 765, 501, 750, 776
See application file for complete search history.

(56) References Cited

U.S. PATENT DOCUMENTS

| | | | | |
|---|---|---|---|---|
| 4,634,290 A | 1/1987 | Rosencwaig et al. | ............ | 374/5 |
| 4,646,088 A | 2/1987 | Inoue | .................... | 340/870.31 |
| 4,854,710 A | 8/1989 | Opsal et al. | ................. | 356/432 |
| 5,074,669 A | 12/1991 | Opsal et al. | ................. | 356/445 |
| 5,206,710 A | 4/1993 | Geiler et al. | ................ | 356/432 |
| 5,408,327 A | 4/1995 | Geiler et al. | ................ | 356/432 |
| 5,978,074 A | 11/1999 | Opsal et al. | .................... | 356/72 |
| 6,081,127 A | 6/2000 | Wagner et al. | ............... | 324/765 |
| 6,583,876 B2 * | 6/2003 | Opsal et al. | ................. | 356/369 |
| 6,671,047 B2 | 12/2003 | Opsal et al. | ................. | 356/369 |
| 6,678,347 B1 | 1/2004 | Kozaczek et al. | ............. | 378/75 |
| 6,693,401 B1 | 2/2004 | Schnetzler et al. | .......... | 318/625 |
| 6,917,039 B2 | 7/2005 | Nicolaides et al. | ....... | 250/341.1 |
| 7,060,980 B2 | 6/2006 | Nicolaides et al. | ....... | 250/358.1 |
| 7,106,446 B2 | 9/2006 | Nicolaides et al. | .......... | 356/445 |
| 7,116,424 B2 | 10/2006 | Nicolaides et al. | .......... | 356/445 |
| 2005/0062971 A1 | 3/2005 | Salnik et al. | ................. | 356/432 |
| 2005/0088187 A1* | 4/2005 | Borden et al. | ............... | 324/752 |
| 2006/0262314 A1* | 11/2006 | Nicolaides et al. | .......... | 356/445 |
| 2007/0188761 A1 | 8/2007 | Salnik et al. | ................. | 356/432 |

\* cited by examiner

*Primary Examiner*—Gregory J Toatley, Jr.
*Assistant Examiner*—Tri T Ton
(74) *Attorney, Agent, or Firm*—Joshua D. Isenberg; JDI Patent

(57) ABSTRACT

The capabilities of the Modulated Optical Reflectance (MOR) technology in dopant metrology applications are combined with the sensitivity of the PhotoReflectance (PR) method in the present system to provide stress and other measurements in semiconductor samples. Such combination enhances the measurement performance of MOR based systems in ion implant applications (implantation dose and energy) and expands system capabilities into a new area of structural parameters measurements, for example, strain in silicon wafers.

30 Claims, 4 Drawing Sheets

COMBINED MODULATED OPTICAL REFLECTANCE AND PHOTOREFLECTANCE SYSTEM

TECHNICAL FIELD

The subject invention relates generally to optical methods for inspecting and analyzing semiconductor wafers and other samples. In particular, the subject invention relates to systems which combine modulated optical reflectance (MOR) with photo-reflectance (PR) to provide improved methods for analyzing semiconductor wafers by increasing the accuracy and flexibility of optical metrology systems.

BACKGROUND OF THE INVENTION

There is a commercial need in the semiconductor industry for metrology equipment that can provide high resolution, nondestructive evaluation of product wafers as they pass through various fabrication stages. A number of systems have been developed for the nondestructive evaluation of semiconductor samples in recent years. One such product is a Modulated Optical Reflectance (MOR) based system. This device incorporates technology described in the following U.S. Pat. Nos. 4,634,290; 4,646,088; 5,854,710; 5,074,669 and 5,978,074. For a better understanding of the MOR technology, each of these patents is incorporated herein by reference.

As described in the above-referenced patents, a basic MOR device includes an intensity modulated pump laser beam which is focused on the surface of a sample for periodically exciting the sample. For semiconductor wafers, thermal and plasma waves are generated in the sample that spread out from the pump beam spot. These waves reflect and scatter off various features and interact with various regions within the sample in a way that alters the flow of heat and/or plasma from the pump beam spot.

The presence of the thermal and plasma waves has a direct effect on the reflectivity at the surface of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be investigated.

A basic MOR system typically includes a second laser for generating a probe beam of radiation. This probe beam is focused collinearly with the pump beam and reflects off the sample. A photodetector is provided for monitoring the power of the reflected probe beam. The photodetector generates an output signal that is proportional to the reflected power of the probe beam and is therefore indicative of the varying optical reflectivity of the sample surface.

The output signal from the photodetector is filtered to isolate the changes that are synchronous with the pump beam modulation frequency. The basic MOR system also includes a lock-in amplifier to monitor the magnitude and phase of the periodic reflectivity signal. This output signal is conventionally referred to as the modulated optical reflectivity of the sample.

In practice, the response of the sample to the pump beam is dependent on the wavelength of the laser. Further, the sensitivity of the system is also dependent on either pump or probe beam wavelength and the relationship between the pump and probe beam wavelengths. The combination of wavelengths selected by the assignee in its commercial embodiment is intended to achieve a balance between the plasma and thermal components of the total MOR signal allowing measurements over a relatively broad range of samples.

In the most common commercial application of MOR, the surface density or dosage levels of implants in silicon are measured. While the pump and probe beam wavelengths in certain existing commercial MOR systems provide good sensitivity across a relatively wide range of doses, certain regions are less sensitive than others due to the limitations inherent in the monochromatic output of lasers. Prior art systems for ion implant metrology used primarily the MOR technology. Commercial systems for ion implant metrology are marketed under the name of Therma-Probe® by KLA-Tencor Corporation of San Jose, Calif.

Early efforts to increase the sensitivity of MOR systems sought to combine MOR with other technologies in a single system. Several combinations of MOR with other technologies, e.g., MOR and Photothermal Radiometry (PTR), MOR and Spectroscopic Ellipsometry (SE), MOR and Spectrometry (a.k.a. Broadband), MOR and Junction Photovoltage (JPV), MOR and Beam Profile Reflectometry (BPR) and others, have been proposed in the prior art to enhance measurement capabilities of the ion implant metrology system. Such combinations are disclosed in the following US patents and patent applications assigned to the assignee of the present invention: U.S. Pat. Nos. 6,671,047; 6,693,401; 6,917,039; 7,060,980; and 6,678,347 and US Patent Application Publication 20070188761. MOR-like systems, which employed a heterodyne approach, as seen in U.S. Pat. Nos. 5,206,710; 5,408,327 and 6,081,127, were also considered in an effort to improve the sensitivity and performance of MOR systems.

It would be a benefit if the user was permitted to select a particular set of wavelengths in MOR system to perform certain measurements. One prior art effort to expand the wavelength measurement capability of a modulated reflectance measurement system is shown in U.S. Pat. No. 7,106,446, which is incorporated by reference in this application. One implementation of the prior art measurement system includes three monochromatic diode-based or diode-pumped semiconductor lasers. Each laser can operate as a probe beam source or as a pump beam source. The laser outputs are redirected using a series of mirrors and beam splitters to reach an objective lens. The objective lens focuses the laser outputs on a sample. Reflected energy returns through the objective lens and is redirected by a beam splitter to a detector. A filter prepares the outputs of the detector for analysis by a processor. Typically, the filter includes a lock-in amplifier that converts the output of the detector to produce quadrature (Q) and in-phase (I) signals for analysis.

The use of three different lasers provides six possible combinations where a single probe beam is used with a single pump beam. Alternately, two lasers can be used to produce different probe beams while the third laser produces the pump beam. In another variation, two lasers can produce pump beams (at different modulation frequencies) while the third produces a probe beam. Another configuration uses all three lasers to produce intensity modulated pump beams. The light reflected by the sample originating from the first laser can be monitored at the difference between the modulation frequencies of the second and third lasers. The reflected light of the second and third lasers is monitored in an analogous fashion. In this way, the prior art system provides a dynamically reconfigurable measurement system that can be optimized to measure a range of different sample types.

For another implementation, the measurement system includes a pump laser and a probe laser. One or both of these lasers are wavelength tunable. The pump laser and probe lasers are controlled by a modulator. An optical modulator is a device which can be used for manipulating a property of light—often of an optical beam, e.g. a laser beam. The type of modulator used is dependent on which property of light is to be controlled, e.g., intensity modulators, phase modulators, polarization modulators, spatial light modulators, etc.

By selectively controlling the wavelengths produced by the pump laser and/or probe laser, the operation of modulated reflectance measurement system can be optimized to measure a range of different sample types.

In some implementations of prior art measurement systems, the pump and probe lasers may be added as modular subsystems. Use of separate low-dose, mid-dose, high-dose, and all-dose modules may expand the range of the system. Each of these modules may include a pump laser and a probe laser having wavelengths that are selected to optimally analyze a particular range of implantation dosages. The all-dose module is intended to provide a wideband tool that operates over a range of dosage levels. The low-dose module, mid-dose module, and high-dose module provide insight into discrete portions of that range. The modules share a set of common components, which typically include optics, a detector and a processor. By selectively enabling or disabling the modules (alone or in combination), the operation of the operation of modulated reflectance measurement system can be optimized to measure a range of different sample types.

Photo-reflectance (PR) technology, while known to be sensitive to structural properties of semiconductor samples, particularly to strain in silicon wafers, was not previously considered to be a viable complement to the MOR technology in a combined system. In MOR, the pump beam is typically modulated at a frequency in the megahertz range. In PR, by contrast, the pump beam is modulated at much lower frequencies, typically in a few Hz to a few kHz range. Moreover, the PR system employs a polychromatic light source to obtain specific strain measurements from the designated sample over a range of wavelengths provided by the source. Measurements associated with an MOR system are specifically limited by the wavelengths of the lasers chosen for use in the system.

It is within this context that embodiments of the present invention arise.

SUMMARY OF THE INVENTION

Embodiments of the present invention provide a combined MOR and photoreflectance system for evaluating a semiconductor sample which includes multiple light sources, including a modulated pump source, at least one light source configured to generate a first output beam of monochromatic light and at least one light source configured to generate a second output beam of polychromatic light. Optical elements of the system are configured to focus the output beams onto the sample. A modulator is coupled to the pump source. The system includes a detector for monitoring the reflected portion of a non-modulated monochromatic beam and generating a first output signal in response thereto that corresponds to the modulated optical reflectivity of the sample. A detector array monitors the reflected portion of a non-modulated polychromatic beam and generates a second output signal in response thereto that corresponds to the photoreflectance of the sample. The system may include a filter to filter out the output signals. A processor controls the modulator to selectively modulate one of the multiple light sources to operate as a pump beam to generate thermal, electrical field, elastic and plasma waves in the semiconductor sample which modulates the optical reflectance coefficient of the sample, wherein either the first and second light source functions as a non-modulated probe beam and the processor evaluates the sample based on the first and second filtered output signals.

BRIEF DESCRIPTION OF THE DRAWINGS

Other objects and advantages of the invention will become apparent upon reading the following detailed description and upon reference to the accompanying drawings in which.

DETAILED DESCRIPTION OF THE PREFERRED EMBODIMENT

Figure 1:
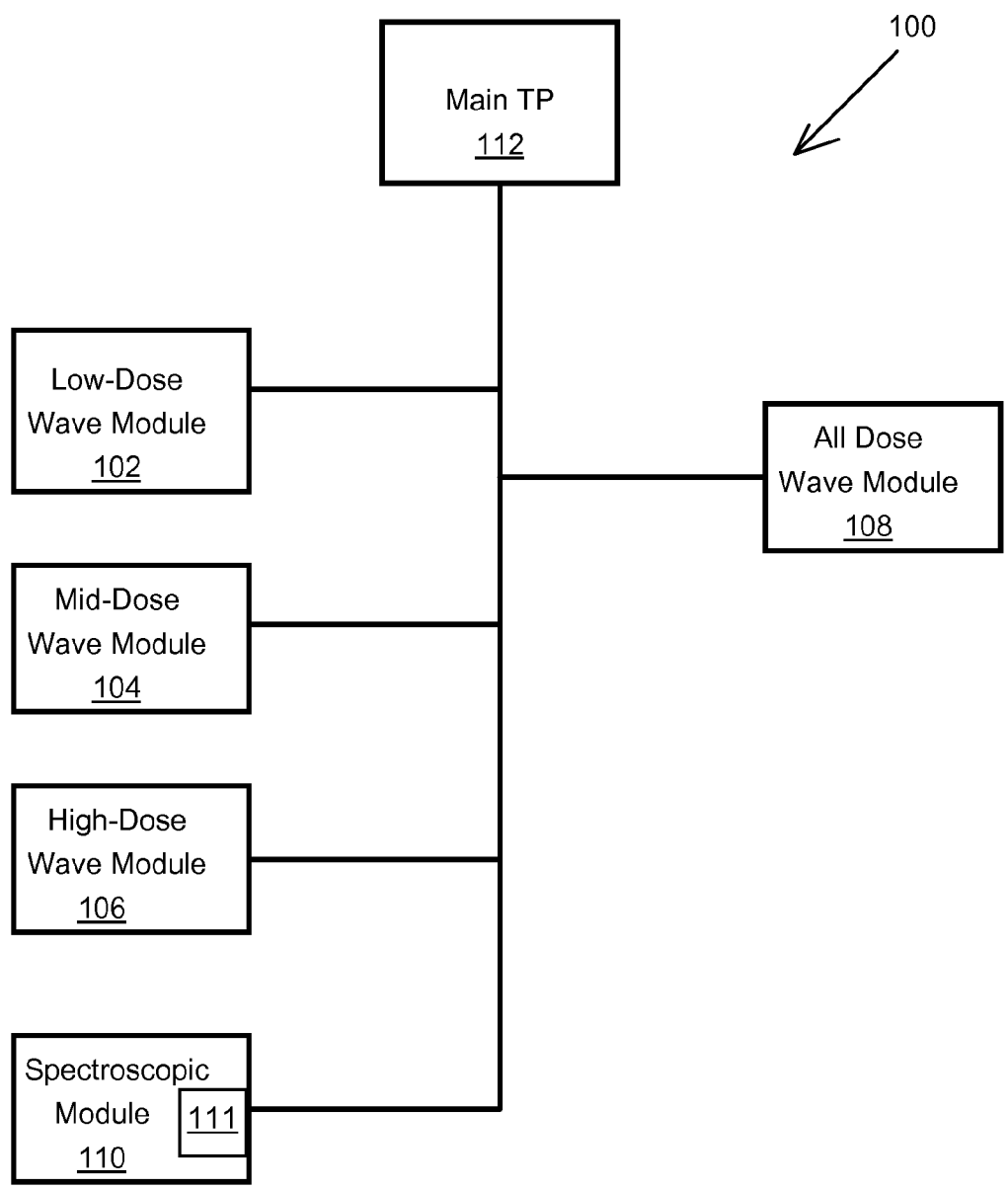
FIG. 1 is a block diagram of a modulated reflectance measurement system that uses four modular laser sources in conjunction with a spectroscopic module in accordance with a preferred embodiment of the present invention.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Embodiments of the current invention relate to a combined Modulated Optical Reflectance (MOR) and PhotoReflectance (PR) measurement system for implant and stress metrology. MOR technology utilizes an intensity modulated pump laser beam to create carrier plasma and thermal waves in a semiconductor sample. A second probe laser beam is reflected from the excited area and the changes in optical reflectance coefficient caused by the propagating plasma and thermal waves are recorded as the MOR signal.

It is particularly desirable to combine the capabilities of the MOR technology in implant metrology applications with the sensitivity of the PR method to provide stress, Silicon-On-Insulator (SOI) and other measurements in semiconductor samples. Such a combination enhances the measurement performance of MOR based systems in ion implant applications (implantation dose and energy) and expands system capabilities into a new area of structural parameters measurements, for example strain in silicon wafers.

PR technology also uses a pump beam and a spectroscopic probe beam. The pump beam creates excess carrier concentration and temperature rise close to the surface of a semiconductor. Changes in reflectivity are recorded as a function of the wavelength of the probe beam. Unlike MOR, PR technology is not wave-based; therefore the pump beam modulation frequency is usually much lower than that in the MOR method.

In the combined MOR and PR system, a pump laser beam may be shared between the MOR and PR modules. A single pump laser may be configured to generate a beam modulated in the hertz to kilohertz range to accommodate the PR technology and a beam modulated in the mega hertz range to accommodate the MOR technology in the combined system. A combined commercial system may consist of several modules optimized for specific applications. For example, it may have a high-dose module and a spectroscopic (stress) module. Alternatively, a combined system may include a low-dose module and a spectroscopic module. The overall system performance can be improved and the number of possible applications can be increased significantly by combining the two measurement technologies together in a single system. It will also be easier and cheaper to manufacture a single combined system as compared to two separate systems. In an alternative embodiment, the spectroscopic probe beam may impinge on the sample surface at normal incidence.

Prior to the present implementation of the combined technology it was considered counter intuitive to attempt such combination due to the different physical nature of the signals in the PR and MOR methods coming from the extreme differences in modulation frequency operating range for the MOR and PR technologies. Unlike the MOR technology, the pump beam in the PR method does not create propagating carrier plasma, thermal and other waves in the sample but rather modulates the properties of the sample under investigation. Furthermore, PR belongs to a class of vibrational spectroscopes which are primarily used in fundamental material research to provide qualitative results about the parameters of the sample. On the other hand, MOR is a precise reflectance measurement technology that requires calibration to other techniques to obtain quantitative measurements of the sample properties.

In a preferred embodiment, a measurement system may comprise several measurement modules optimized for different applications: high-, middle-, and low-dose modules as well as an implant monitoring apparatus and including a spectroscopic module based on the PR technology. Each module may have its own combination of pump and probe beam wavelengths. Pump and probe beam producing lasers may be shared and interchanged between different modules. By way of example, the pump beam wavelengths may range from 350 nm to 850 nm.

In FIG. 1, an example of the combined modulated reflectance measurement system of the present invention is shown schematically and generally designated 100. For this system, pump and probe lasers may be added as modular subsystems. The example illustrated in FIG. 1 shows four of these modular subsystems. However, any number of modules may be used. In order, the four modular subsystems include a low-dose module 102, a mid-dose module 104, a high-dose module 106, and an all-dose module 108.

Low-, high- and mid-dose modules may use different combinations of the pump and probe beam wavelengths, different intensities of the pump and probe beams and different pump beam modulation frequencies.

Providing the PR technology for the combined system 100 is a spectroscopic module 110. The spectroscopic module 110 includes a polychromatic light source 111. The polychromatic light source may be a suitable lamp, such as a Xenon arc lamp. The polychromatic light source 111 preferably produces radiation in a wavelength range suitable for photoreflectance. In particular, photoreflectance is based on probing for the modulation of the physical properties of the sample (e.g. bandgap energy, position of the fundamental absorption peaks, etc.). Therefore, it is desirable for the polychromatic light source 111 to produce a beam of probe radiation having wavelengths that are sensitive to such variations in physical properties of the sample. The wavelength range may vary depending on the nature of the target that is being probed.

Each of the modules 102, 104, 106 and 108 includes a pump laser and a probe laser. For MOR, the probe lasers for these modules may produce probe beams that are sensitive to plasma or thermal waves induced in a target by the modulated pump beam. In general, longer wavelengths tend to be more sensitive to the plasma waves while short probe wavelengths are more sensitive to thermal waves in the sample. The probe wavelength ranges for sensing preferably thermal and plasma waves may very depending on the physical properties of the sample.

The probe beams from the modules 102, 104, 106, 108 may have wavelengths that are selected to optimally analyze a particular range of implantation dosages. At low implantation doses, the MOR signal is more likely to be driven by the plasma waves while at high implantation doses the MOR signal is driven by the thermal waves.

The all-dose module 108 is intended to provide a wideband tool that operates over a range of dosage levels which is encompassed by the modules 102, 104 and 106. The low-dose module 102, mid-dose module 104, and high-dose module 106 provide insight into discrete portions of that range. The spectroscopic module 110 provides reflectivity measurements over the range of wavelengths provided by a polychromatic light source of the spectroscopic module 110. An optical platform 112 may provide a set of common components (e.g.: a sample mount, optics that couple the pump beams and probe beams from the various modules to the sample, filter, optics that couple probe radiation reflected from the sample to a detector, the detector, and processor) used by each of the modules 102, 104, 106, 108 and 110. By way of example the optical platform 112 may be a Therma-Probe platform available from KLA-Tencor Corporation of San Jose, Calif.

For the example of FIG. 1, the different modules are intended to analyze different implantation dosage ranges. It should be appreciated that this is a representative implementation. Modules could also be selected to analyze other features, such as a range of modules designed to analyze different ultra shallow junctions (USJ) and other structures and devices.

By way of example, a spectroscopic module based on PR technology may share a laser pump beam with one or more implant modules that use MOR technology. A broadband light source of the spectroscopic module may produce a probe light beam that is focused on an area on the surface of the sample excited by the pump laser beam and engages the sample at an angle of incidence. A reflected portion of the broadband probe light beam may be detected by an array of photodetectors to produce a PR signal as a function of wavelength of the probe beam.

Figure 2:
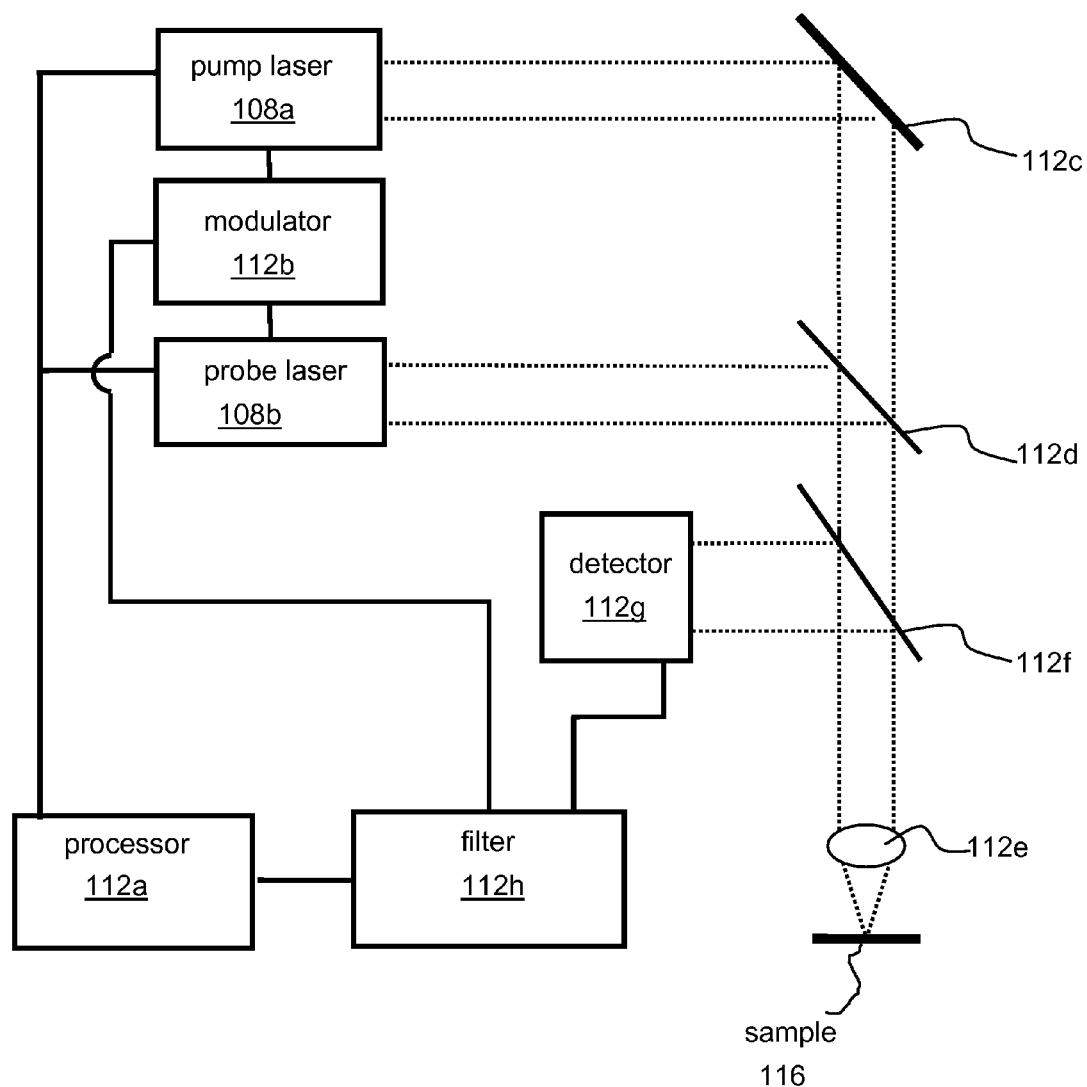
FIG. 2 is a block diagram of a representative dosage module of FIG. 1 that uses two wavelength tunable laser sources.

In FIG. 2, a schematic diagram of a representative dosage module is shown. While the all dose wave module 108 has been chosen for illustrative purposes, all of the dosage modules 102, 104, 106 and 108 may be similarly configured. As shown in FIG. 2, the all dose wave module 108 includes two monochromatic light sources, e.g., a pump laser 108*a* and a probe laser 108*b*. At least one, and for some implementations both, of these lasers may be wavelength tunable. Preferably, the output can be tuned over a range of at least 50 nm. Pump laser 108*a* and probe laser 108*b* may be controlled by a processor 112*a*, which is part of the component set 112 shown in FIG. 1. The time varying characteristics of the output of pump laser 108*a* may be controlled by a modulator 112*b*, which may also be part of the component set 112. The modulator 112*b* may take one of several forms. An electro-optic modulator (EOM) is an optical device in which a signal-controlled element displaying electro-optic effect is used to modulate a beam of light. The modulation may be imposed on the phase, frequency, amplitude, or direction of the modulated beam. Modulation bandwidths extending into the gigahertz range are possible with the use of laser-controlled modulators. An acousto-optic modulator (AOM), also called a Bragg cell, uses the acousto-optic effect to diffract and shift the frequency of light using sound waves (usually at radio-frequency). A piezoelectric transducer is attached to a material such as glass. An oscillating electric signal drives the transducer to vibrate, which creates sound waves in the glass. These can be thought of as moving periodic planes of expansion and compression that change the index of refraction. In a preferred embodiment of the combined MOR/PR system a modulator 112b controls the output of a single pump laser 108a to generate an output beam to excite the sample in the hertz to kilohertz range to accommodate the PR technology and an output beam in the megahertz range to accommodate the MOR technology.

It is noted that the modulator 112b may be selectively coupled to both of two lasers so that either of the two lasers may selected to act as the pump laser 108a and the laser not selected to act as the pump laser may act as the probe laser 108b. Furthermore, each of the dose modules 102, 104, 106, 108 may be similarly configured. Such a configuration allows for a greater range of pump and probe wavelengths in the combined system 100.

The output of pump laser 108a and probe laser 108b may be redirected by a mirror 112c and a beam splitter 112d, respectively. After being redirected, the two outputs may pass through an objective lens 112e and are focused on a sample 116. The reflected energy returns through the objective lens 112e and is redirected by a beam splitter 112f towards a detector 112g. Detector 112g measures the energy of probe radiation reflected by sample 116 and forwards a corresponding signal to a filter 112h. The filter 112h may include a lock-in amplifier that uses the output of detector 112g as a signal input, and the output of modulator 112b as a reference input to produce a filtered output signal. The filtered output signal corresponds to a portion of probe radiation reflected from the surface of a sample that is affected by the pump beam. The filtered output may include quadrature (Q) and in-phase (I) signals for analysis. Processor 112a may convert the Q and I signals to amplitude and/or phase values to analyze the sample. In other cases, the Q and I signals may be processed directly. By selectively controlling the wavelengths produced by pump laser 108a and/or probe laser 108b, the operation of all dose wave module 108 may be optimized to match the characteristics of sample 116. Each of the modules 102, 104, 106 and 108 may use a set of common components 112a-112h, e.g., modulator, optics, filter, processor, et al., designated as the optical platform 112 in FIG. 1.

Figure 3:
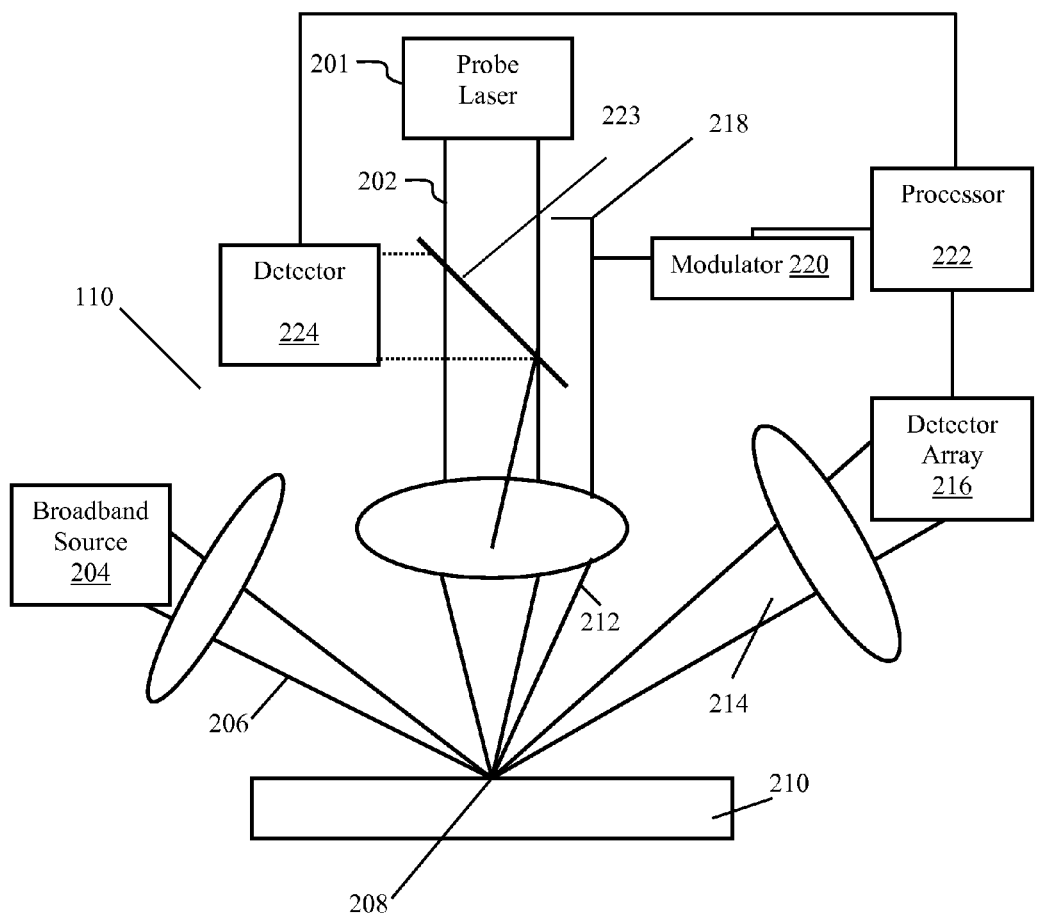
FIG. 3 is a schematic diagram of the combined modulated reflectance measurement system of the present invention with a spectroscopic probe disposed at an angle of incidence.

A schematic representation of a preferred embodiment of the present invention is shown in FIG. 3. In FIG. 3, a spectroscopic module 110 based on the PR technology may share certain optical components with one or more implant modules that use the MOR technology. In particular the spectroscopic module 110 may be incorporated into the same system that contains the dosage modules 102, 104, 106, 108. One of these modules may include a probe laser 201 that produces a probe beam 202 and a pump laser 218 that produces a pump beam 212. A modulator 220 may modulate the pump beam at some known reference modulation frequency. A broadband light source 204 of the spectroscopic module 110 may produce a probe beam of polychromatic light 206 that is focused on an area 208 on the surface of a sample 210 excited by a modulated pump laser beam 212 and engages the sample 210 at an oblique angle of incidence. The pump laser beam 212 and probe beam 202 (or the probe beam from the broadband source 204) may be focused onto substantially the same location on the sample 210. As used herein the expression "onto substantially the same location" mean that the probe beams overlap to some extent with the pump beam where the beams intersect the surface of the sample 210. A reflected portion of the broadband probe light beam 214 is detected by an array of photodetectors 216 producing a PR signal as a function of wavelength of the probe beam 206. A beam splitter 223 may direct a portion of the probe beam 202 that is reflected from area 208 on the surface of the sample 210 towards a detector 224.

In the combined MOR and PR system, the pump laser beam 212 may be shared between an MOR module and a PR module. The modulator 220 may modulate the pump beam 212 at a modulation frequency of a hertz to a few kilohertz to accommodate the PR technology. The modulator may 220 may modulate the pump beam at a modulation frequency of at least one megahertz to accommodate the MOR technology. A processor 222 (e.g., a general purpose computer) may be coupled to the detector array 216 and/or detector 224 and the modulator 220. The processor may be configured (e.g., by suitable programming) to control the modulator 220 to selectively modulate the pump beam at different modulation frequency ranges to generate thermal and plasma waves in different proportions in the sample 210. The processor may also be configured to evaluate the sample based on output signals from the detector array 216 and/or detector 224. The processor 222 may implement a signal filter, such as a lock-in amplifier to extract a pump beam modulated component from the detector or detector array signal. Alternatively, the lock-in amplifier may be implemented by a separate component that is coupled to the processor.

Figure 4:
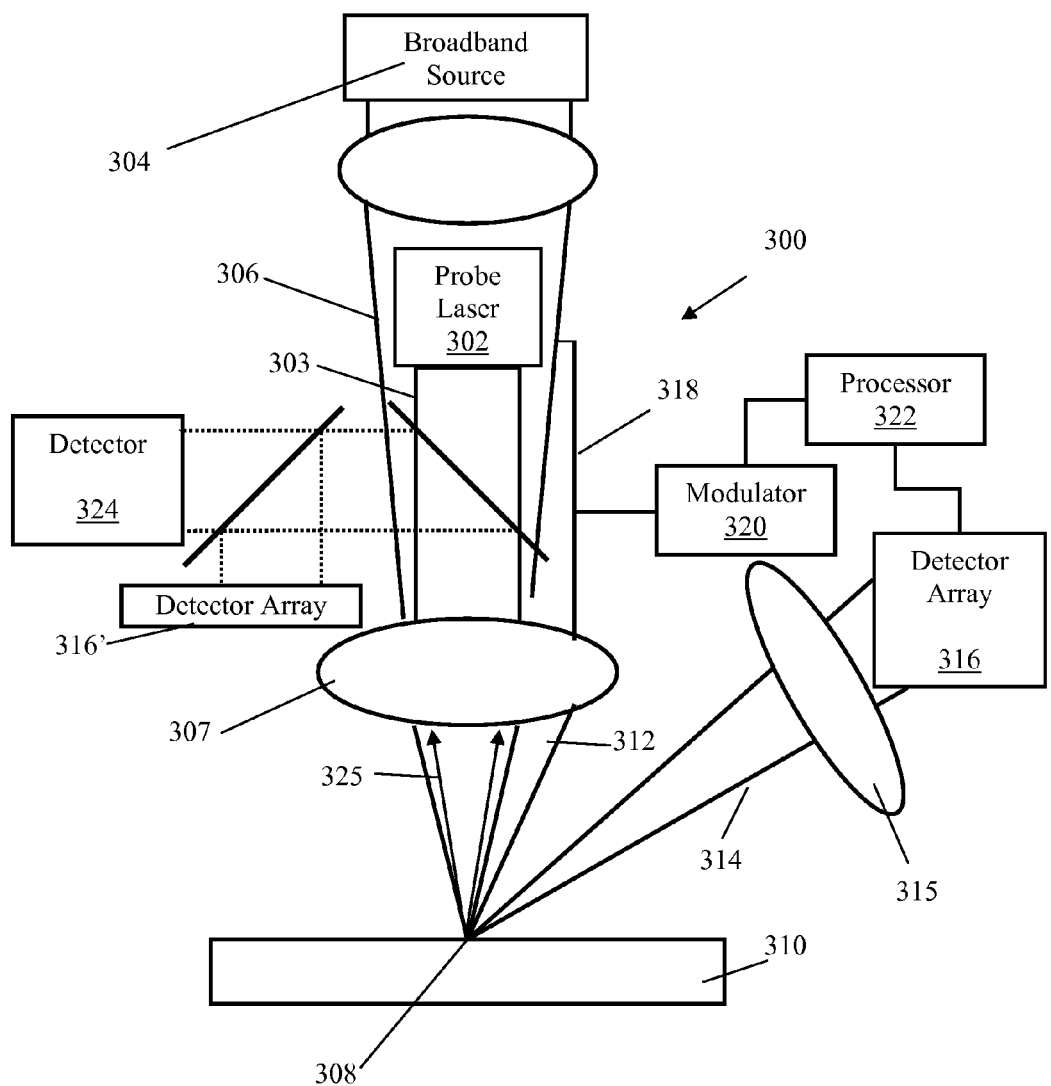
FIG. 4 is a schematic diagram of an alternative embodiment of the combined modulated reflectance measurement system of the present invention with a spectroscopic probe disposed at normal incidence.

In an alternative embodiment shown schematically in FIG. 4, the spectroscopic probe beam may impinge on the sample surface at normal incidence. In FIG. 4, a system 300 may include a probe laser 302 and a spectroscopic module having a broadband light source 304. The laser 302 may be a component of one or more of the dosage modules 102, 104, 106, 108 in FIG. 1. The laser 302 may produce a monochromatic probe beam 303. The broadband light source 304 may be a component of the spectroscopic module 110 shown in FIG. 1. The broadband light source may produce a probe beam 306 of polychromatic light that is focused on an area 308 on the surface of a sample 310. Both probe beams 303, 306 may be coupled to probe optics 307 that focus the beams onto the area 308 at normal incidence with respect to the surface of the sample 310. The area 308 is also excited by pump radiation 312 from a pump laser 318. The pump 318 laser may be a component of one of the dosage modules indicated in FIG. 1. The reflected broadband probe light beam 314 may be collected by detection optics 315 and detected by an array of photodetectors 316 producing a PR signal as a function of wavelength of the probe beam 306. A reflected portion 325 of the monochromatic probe beam 303 may be collected by the probe optics 307 and coupled to a detector 324. In some embodiments, the reflected broadband probe beam light 314 may be reflected back towards the probe optics 307 and selectively coupled to the detector 324 or a detector array 316'. Signals from the detector array 316, 316' or detector 324 may be coupled to a processor 322 for analysis. The spot size of the polychromatic beam from the broadband source 304 may be smaller in normal incidence than for an oblique incidence system.

Embodiments of the present invention combine the capabilities of the MOR technology in implant metrology applications with the sensitivity of the PR method to provide stress, SOI and other measurements in semiconductor samples. Such combination can enhance the measurement performance of MOR based systems in ion implant applications (implantation dose, energy, angle of incidence, etc.) and expands system capabilities into a new area of structural parameters measurements, including strain in silicon wafers.

While the above is a complete description of the preferred embodiment of the present invention, it is possible to use various alternatives, modifications and equivalents.

Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A system for evaluating a semiconductor sample comprising:
   two or more light sources, including at least one light source configured to generate a first output probe beam of monochromatic light and at least one light source configured to generate a second output probe beam of polychromatic light,
   a pump laser configured to generate a pump beam;
   a modulator configured to modulate the pump beam to produce an intensity-modulated pump beam, wherein the modulator is configured to modulate the pump beam at a frequency over a range from 1 Hz to 1 kHz for photoreflectance measurements and greater than 1 MHz for modulated optical reflectivity measurements;
      optical elements configured to focus the intensity-modulated pump beam and the first and second output probe beams onto substantially the same location on a surface of the sample;
   a detector configured to receive a portion of the first output probe beam that is reflected from the surface of the sample and generate a first output signal in response thereto that corresponds to a modulated optical reflectivity of the sample;
   a detector array configured to receive a reflected portion of the second output probe beam that is reflected from the surface of the sample and generate a second output signal in response thereto that corresponds to a photoreflectance of the sample;
   a processor coupled to at least one of the detector or the detector array said processor configured to evaluate the sample based on the first and second output signals.

2. The system of claim 1, further comprising a filter coupled to at least one of the detector or detector array, modulator and processor, wherein the filter is configured to produce a filtered output signal.

3. The system of claim 2, wherein the filtered output signal corresponds to a portion of the first or second output signal that is characterized by modulation that is related to modulation of the modulated pump beam.

4. The system of claim 3, wherein the filtered output signal includes an in-phase (I) signal and a quadrature (Q) components of the signal.

5. The system of claim 1, wherein the two or more light sources comprise a series of illumination modules including at least one illumination module having a pump laser configured to produce an intensity modulated output and a probe laser configured to produce a non-modulated output, the pump and probe laser in each module chosen to optimize measurement within a particular implantation dosage range.

6. The system of claim 5, wherein the at least one illumination module comprises a spectroscopic module including a source of the polychromatic light and directs an output beam at the sample at an incident angle.

7. The system of claim 5, wherein at least one illumination module comprises a spectroscopic module including a source of the polychromatic light and directs an output beam at the sample at normal incidence.

8. The system of claim 5, wherein the series of illumination modules includes separate modules for high, medium and low implantation dosage ranges as well as an overall module that spans the combined range of the high, medium and low modules.

9. The system of claim 8, wherein the illumination modules may be operated in any combination.

10. The system of claim 9, wherein a pump laser of a dosage module is shared with the spectroscopic module.

11. A method for evaluating a semiconductor sample comprising:
   generating a first output beam of monochromatic light and generating a second output beam of polychromatic light from two or more light sources;
   focusing the first and second output beams onto an area of the sample;
   coupling a modulator to said two or more light sources;
   selectively modulating a pump beam and exciting the area of the sample with a pump beam, wherein the modulator is configured to modulate the pump beam at a frequency over a range from 1 Hz to 1 kHz for photoreflectance measurements and greater than 1 MHz for modulated optical reflectivity measurements;
   generating a first output signal in response to a reflected portion of the polychromatic light, wherein the first output signal corresponds to a modulated optical reflectivity of the sample;
   generating a second output signal in response to a reflected portion of the polychromatic beam, wherein the second output signal corresponds to a photoreflectance of the sample; and
   evaluating the sample based on the first and second output signals.

12. The method of claim 11, including the step of filtering out the first and second output signals to produce a filtered output signal.

13. The method of claim 12, wherein evaluating the sample includes evaluating the sample based on the filtered output signal.

14. The method of claim 12, wherein the filtered output signal corresponds to a portion of the first or second output signal that is characterized by modulation that is related to modulation of the modulated pump beam.

15. The method of claim 11, wherein the two or more light sources comprise a series of illumination modules and at least one illumination module is configured to produce an intensity modulated output and a non-modulated output, with the pump and probe laser in each module chosen to optimize measurement within a particular implantation dosage range.

16. The method of claim 15, wherein focusing the output beams includes directing the second output beam at the sample at an oblique incident angle.

17. The method of claim 15, wherein focusing the output beams includes directing the second output beam at the sample at normal incidence.

18. The method of claim 15, wherein the series of illumination modules includes separate modules for high, medium and low implantation dosage ranges as well as an overall module that spans the combined range of the high, medium and low modules.

19. The method of claim 18, including operating the illumination modules in any combination.

20. The method of claim 19, wherein a dosage module shares its pump laser with a spectroscopic module.

21. An apparatus for evaluating a semiconductor sample comprising:

multiple illumination modules, with at least one illumination module configured to generate a first output beam of monochromatic light, at least one illumination module configured to generate a second output beam of monochromatic light; and at least one illumination module configured to generate a third output beam of polychromatic light;

a modulator configured to selectively modulate at least one of the first or second output beam, wherein the modulator is configured to modulate the third output beam at a frequency over a range from 1 Hz to 1 kHz for photoreflectance measurements and greater than 1 MHz for modulated optical reflectivity measurements;

optical elements configured to focus the first, second and third output beams onto substantially the same location at a surface of the sample;

a detector configured to generate a first output signal in response a portion of the first or second output beam that is reflected from the location at the surface of the sample, wherein the first output signal corresponds to a modulated optical reflectivity of the sample, wherein the modulated optical reflectivity depends on plasma waves in the semiconductor sample;

a detector configured to generate a second output signal in response a portion of the third output beam that is reflected from the location at the surface of the sample, wherein the second output signal corresponds to a photoreflectance of the sample; and a processor configured to control the modulator to selectively modulate one of the first and second beams to operate as a pump beam, wherein either the other of the first and second output beams or the third output beam functions as a probe beam and wherein the processor is configured to evaluate the sample based on the first and second output signals.

22. The apparatus of claim 21 further including a filter configured to filter the first and second output signals.

23. The apparatus of claim 22, wherein the processor is configured to evaluate the sample based on the filtered output signal.

24. The apparatus of claim 22, wherein the filtered output signal corresponds to a portion of the first or second output signal that is characterized by modulation that is related to modulation of the modulated pump beam.

25. The apparatus of claim 21, wherein at least one illumination module is configured to include a pump laser producing an intensity modulated output and a probe laser producing a non-modulated output, the pump and probe laser in each module chosen to optimize measurement within a particular implantation dosage range.

26. The apparatus of claim 25, wherein at least one module comprises a spectroscopic module which is the source of polychromatic light and directs an output beam at the sample at an incident angle.

27. The apparatus of claim 25, wherein at least one module comprises a spectroscopic module which is the source of polychromatic light and directs an output beam at the sample at normal incidence.

28. The apparatus of claim 25, wherein the series of illumination modules includes separate modules for high, medium and low implantation dosage ranges as well as an overall module that spans the combined range of the high, medium and low modules.

29. The apparatus of claim 28, wherein the illumination modules may be operated in any combination.

30. The apparatus of claim 28, wherein the pump laser of a dosage module is shared with the spectroscopic module.

\* \* \* \* \*